United States Patent
Le

(10) Patent No.: US 11,440,827 B2
(45) Date of Patent: Sep. 13, 2022

(54) METHOD FOR THE PREPARATION OF BIOPOLYMERS

(71) Applicant: UNITED UTILITIES PLC, Warrington (GB)

(72) Inventor: Minh Son Le, Warrington (GB)

(73) Assignee: UNITED UTILITIES PLC, Warrington (GB)

(*) Notice: Subject to any disclaimer, the term of this patent is extended or adjusted under 35 U.S.C. 154(b) by 29 days.

(21) Appl. No.: 16/051,742

(22) Filed: Aug. 1, 2018

(65) Prior Publication Data

US 2018/0340007 A1    Nov. 29, 2018

Related U.S. Application Data

(63) Continuation of application No. 15/109,052, filed as application No. PCT/EP2015/050067 on Jan. 5, 2015, now abandoned.

(30) Foreign Application Priority Data

Dec. 30, 2013  (GB) ..................................... 1323123

(51) Int. Cl.
| | |
|---|---|
| C02F 11/00 | (2006.01) |
| C12N 15/10 | (2006.01) |
| C07K 1/14 | (2006.01) |
| C07K 1/30 | (2006.01) |
| C07K 9/00 | (2006.01) |
| C02F 1/36 | (2006.01) |
| C02F 1/54 | (2006.01) |

(52) U.S. Cl.
CPC ............... *C02F 11/00* (2013.01); *C07K 1/14* (2013.01); *C07K 1/30* (2013.01); *C07K 9/00* (2013.01); *C12N 15/1003* (2013.01); *C02F 1/36* (2013.01); *C02F 1/54* (2013.01); *C02F 2303/06* (2013.01); *C02F 2303/26* (2013.01); *Y02W 10/40* (2015.05)

(58) Field of Classification Search
None
See application file for complete search history.

(56) References Cited

U.S. PATENT DOCUMENTS 7,909,995 B2 * 3/2011 Jiang .................. B01D 53/1468
                                                    210/206

OTHER PUBLICATIONS

Clarke et al. "Biopolymer yields from activated sludge and their relation to the operation of treatment plant", Biotechnology Letters, 1982, vol. 4, No. 10, pp. 655-660.*
Braun et al. "Development and Application of an Enzymatic and Cell Flotation Treatment for the Recovery of Viable Microbial Cells from Environmental Matrices Such as Anaerobic Sludge". Applied and Environmental Microbiology, Dec. 2011, vol. 77, No. 24, p. 8487-8493.*
Shimizu et al. "Anaerobic waste activated sludge digestion, a bioconversion mechanism and kinetic model", Biotechnology and Bioengineering, 1993, vol. 41, pp. 1082-1091.*
Fytili et al: "Utilization of sewage sludge in EU application of old and new methods—A review", Renewable and Sustainable Energy Reviews, Elseviers Science, New York, NY, US, vol. 12, No. 1. Oct. 9, 2007 (Oct. 9, 2007), pp. 116-140.
J.W. Morgan et al: "A comparative study of the nature of biopolymers extracted from anaerobic and activated sludges", Water Research, vol. 24, No. 6, Jun. 1, 1990 (Jun. 1, 1990), pp. 743-750.
Liu Xiaoling et al: "Enhancement of solubilization and acidification of waste activated sludge by pretreatment", Waste Management, vol. 28, No. 12, May 27, 2008 (May 27, 2008), pp. 2614-2622.
Marjoleine P. J. Weemaes et al: "Evaluation of current wet sludge disintegration techniques", Journal of Chemical Technology & Biotechnology, vol. 73, No. 2, Oct. 1, 1998 (Oct. 1, 1998), pp. 83-92.

* cited by examiner

*Primary Examiner* — Vera Afremova
(74) *Attorney, Agent, or Firm* — Innovation Capital Law Group, LLP; Vic Lin

(57) ABSTRACT

A method of preparing and separating biopolymers and biopolymer fractions is useful for wastewater treatment applications from sewage sludge. The method comprising the steps of disrupting the bacterial cell walls of bacteria present in the sewage sludge by at least 75% to release the intracellular contents of the bacterial cells and separating the biopolymers from any contaminants present.

26 Claims, No Drawings

METHOD FOR THE PREPARATION OF BIOPOLYMERS

CROSS-REFERENCE TO RELATED APPLICATIONS

This application is a continuation of U.S. patent application Ser. No. 15/109,052, filed Jun. 29, 2016, which is a national stage application under 35 USC 371 of PCT application number PCT/EP2015/050067 filed Jan. 5, 2015, which claims benefit to GB Application No. 1323123.8 filed Dec. 30, 2013, the contents of each of which are herein incorporated by reference.

BACKGROUND OF THE INVENTION

The present invention relates to a method of preparing and separating biopolymers and biopolymer fractions from sewage sludge. In particular, the present invention relates to the preparation and separation of biopolymers and biopolymer fractions which are derived from micro-organisms, especially micro-organisms or biomass arising from wastewater treatments. Such wastewater treatments include for example activated sludge processes which are commonly used for the treatment of municipal sewage.

Such sludges may contain biopolymers or biopolymer fractions in the form of peptidoglycan or deoxyribonucleic acid (DNA) fractions or a combination of these two materials.

The biomass which arises from the treatment of wastewater generated in households, commercial properties and industry is commonly known as sewage sludge. That is, the term sewage sludge refers to sludge which has not been subjected to a digestion stage, whilst biological sludge is a sludge that is generated from the biological treatment of sewage.

In Europe, the treatment of sewage sludge follows the Urban Wastewater Treatment Directive (91/271/EEC). Annual sludge production currently stands at 1.3 M tonnes for the UK and 10M tonnes for Europe. Globally, the volume of sludge is expected to increase significantly over the coming years as many of the developing economies start to implement their own pollution control measures. Consequently, sewage sludge will need to be either:
  i) treated to provide a source of energy and valuable raw materials which may be recovered for useful applications; or
  ii) destroyed to prevent pollution.

Presently there are only two practical options for sludge management, namely agricultural recycling or incineration. Agricultural recycling is regarded as the best practicable environmental option. Incineration, on the other hand, is much more costly and socially objectionable. However, incineration is still preferred due to the possible risks arising with agricultural recycling.

The most common method of sludge treatment is digestion, specifically anaerobic digestion, which recovers the energy content of the sludge as biogas and reduces the odour and pathogen level of the sludge to make it suitable for agricultural recycling. In general, anaerobic digestion comprises a series of complex biochemical reactions mediated by a consortium of micro-organisms that convert organic compounds into methane and carbon dioxide. Anaerobic digestion is also a stabilization process, achieving odour, pathogen, and mass reduction.

The digested sludge residue arising from anaerobic digestion primarily comprises various types of bacteria and hence bacterial cells. Bacterial cells represent a huge untapped resource globally.

Most bacteria in sludge are gram-negative, and in activated sludge account for over 90% of the bacteria strains. Gram negative bacteria possess a relatively 'thin' cell wall consisting of only a few layers of peptidoglycan which comprises about 10% of the biomass of the bacteria.

Peptidoglycan (also known as murein) is a unique biopolymer which consists of both D- and L-amino acids. The basic structure of peptidoglycan consists of a carbohydrate backbone of alternating residues of $\beta$-(1,4) linked N-acetyl glucosamine and N-acetyl muramic acid. Attached to the N-acetyl muramic acid is a peptide chain of 3 to 5 amino acids. The peptide chain can be cross-linked to another peptide chain on another carbohydrate strand forming a 3-D mesh-like layer.

In contrast, the intracellular components DNA and RNA account for about 23% of the dry mass of a bacteria cell. The remainder of the biomass, that is, the 67% of the dry mass that constitutes the bacteria cell, includes for example polysaccharides, proteins and phospholipids. The polysaccharides, proteins and phospholipids which are found largely outside the cell wall are often referred to as the extracellular polymeric substances (EPS). The EPS typically account for 50% of cell biomass.

Both DNA and RNA are biopolymers composed of repeating units of nucleotides. Each nucleotide consists of a sugar, a phosphate and a nucleic acid base. The bases are hydrophobic and relatively insoluble in water at the near neutral pH of the cell. At acidic or alkaline pH they become charged, and their solubility in water increases. The interactions between DNA and metals, particularly heavy metals, have been extensively studied. The binding of metals to the nucleic acids generally occurs through the formation of complexes. DNA therefore acts as a biological ligand for metals and may associate with metals after cell lysis.

Exciting possibilities have been suggested for the use of biopolymers and biopolymer fractions isolated from sewage sludge. For example, it has been mooted that biopolymers and biopolymer fractions from sewage sludge could be employed as substitutes for polymers and copolymers commonly used as flocculants/coagulants in municipal and industrial wastewater treatment.

Alternatively, biopolymers and biopolymer fractions have been suggested as potentially useful products for wastewater treatment and the removal of undesirable contaminants such as heavy metals or valuable commodities such as phosphorus.

However, hitherto there are no known methods for commercial manufacture of biopolymers and the efficacy of their use in any of the suggested applications so far has never been demonstrated in practice.

Nevertheless, if new methods were available to enable the biopolymers to be recovered, preferably in a relatively pure form, the biopolymers and biopolymers fractions would potentially provide a viable income for sludge producers and, more importantly, a new option for sludge management.

Therefore there exists the need for a suitable method for the preparation of biopolymers and biopolymer fractions from sewage sludge.

More particularly there exists the need for a method of preparing biopolymers and biopolymer fractions which also allows the isolation and separation of biopolymers and biopolymer fractions from sewage sludge.

SUMMARY OF THE INVENTION

It is therefore an aim of the present invention to provide a method for the preparation and separation of biopolymers and biopolymer fractions from sewage sludge which addresses the requirements of the industry.

It is a further aim of the present invention to provide a new and improved method for the preparation and separation of biopolymers and biopolymer fractions from sewage sludge which is both effective and efficient and which may be applied to wastewater treatment applications.

DETAILED DESCRIPTION OF THE INVENTION

According to a first aspect of the present invention there is provided:

a method of preparing and separating biopolymers and biopolymer fractions from sewage sludge, the method comprising the following steps:

i) disrupting the bacterial cell walls of bacteria present in the sewage sludge by at least 75% to release the intracellular contents of the bacterial cells; and ii) separating the biopolymers from any contaminants present.

In step (i) of the method of the invention at least 75% of the total amount of cells present are ruptured, that is, cells are ruptured by at least 75% to release their contents. Preferably, the bacterial cell walls may be disrupted by at least 85% to release the intracellular contents of the bacterial cells, more preferably by at least 90%, even more preferably by 95% and most preferably by 99%. That is, the higher the degree of rupture the more biopolymers are available for recovery.

In step (i) the intracellular contents of the bacterial cells are released so as thereby to free soluble biopolymers in the form of a cell lysate. The biopolymers separated by the process may be soluble biopolymers in the cell lysate or may be insoluble biopolymers present in the cell lysate.

The method of the present invention may further comprise the step of:

removing extracellular polymeric substances (EPS) from the bacterial cells in the sewage sludge prior to disrupting the bacterial cell walls.

The method of the present invention may also further comprise the step of:

precipitating the soluble biopolymers from the cell lysate prior to separating the biopolymers from any contaminants present. The soluble biopolymers precipitated preferably comprise nucleic acids.

Alternatively, the cell lysate may be anaerobically digested to decompose nucleic acids so that insoluble peptidoglycan present in the cell lysate may be separated and isolated.

The method of the present invention may preferably be used with known and readily available equipment which requires minimal cost to implement.

The method of the present invention is therefore also suitable for large scale industrial biopolymer production in quantities commensurate with the operation of a municipal sewage treatment works and therefore provides an answer to the problem of how to manage the ever increasing problem of sewage waste.

It will be understood that the term 'sludge' referred to herein refers to the solid fractions found in wastewater and sewage and which arise from the treatment of the wastewater and sewage.

Typically in the treatment of municipal sewage the wastewater is subjected to a sedimentation process wherein a certain amount of suspended solids settle out under the effect of gravity yielding a first sludge fraction known as 'primary sludge'.

The settled wastewater containing mainly dissolved organic substances and nutrients is subsequently treated biologically in a second process commonly known as the 'activated sludge process'.

Sludge from the second process is known as 'biological sludge' which is mostly made up of bacterial cells whereas the primary sludge contains mainly food residue and other inert inorganic components such as silt and fine sand.

The biological sludge fraction and primary sludge fraction are often combined to provide combined sludge or co-settled sludge. The combined sludge from the treatment of municipal sewage typically contains between 40 to 60% weight/weight (w/w) of biological sludge. A typical sludge matrix may therefore comprise 35% biological sludge, 35% primary sludge and 30% inert inorganic matter on a dry weight basis.

It is preferred that in the method of the present invention the sewage sludge is a biological sludge, i.e. the sludge obtained by means of the second process known as the activated sludge process.

In addition, in relation to the method of the present invention the ruptured bacterial cell walls may be ground to disperse or dissolve the peptidoglycan.

The extracellular polymeric substances (EPS) may be removed using a mechanical means, or alternatively the EPS may be removed using chemical means or enzyme treatments. For example, the EPS may be dislodged from the cell wall by treatment with a shearing device or a low power ultrasonic device before anaerobic digestion.

Also in relation to the method of the present invention the cell walls may be disrupted using one or more of: ultrasonication, and/or bead mills and/or caustic treatments. For convenience, cell rupture should be performed after EPS removal to minimise contamination of the biopolymers.

It is preferred that in the method of the present invention the peptidoglycan present in the cell lysate is separated and isolated from the cell DNA.

When peptidoglycan is the desired product, the cell lysate is preferably anaerobically digested to destroy the DNA and in addition, the cell lysate is preferably filtered after digestion to recover the peptidoglycan.

It is known in the art that large molecules such as biopolymers have surfaces and their surfaces can have affinity for water or oil or certain chemicals. The nature of the surfaces of the biopolymers is referred to as their surface properties. In relation to the method of the present invention the biopolymers and fractions may be treated before, during or post the precipitation step with one or more chemicals to alter or enhance the surface property of the biopolymers and improve the binding of specific compounds to the biopolymers and fractions.

The DNA and/or peptidoglycan isolated using the method the present invention may be used as flocculants and coagulants and as a replacement for known flocculants and coagulants.

According to a second aspect of the present invention there is provided a method for the preparation and separation of biopolymers and biopolymer fractions from sewage sludge, the method comprising the following steps:

i) removing extracellular polymeric substances (EPS) from bacteria cells in the sewage sludge;

ii) disrupting the bacterial cell walls by at least 75% to release the intracellular contents of the bacterial cells;

iii) precipitating soluble biopolymers to form a cell lysate and separating the biopolymers from any contaminants present.

According to a third aspect of the present invention there is provided the use of the DNA and/or peptidoglycan isolated using the method according to the first or second aspect of the present invention as flocculants and coagulants.

The biopolymer preparation using the methods according to the present invention enables the recovery of biopolymer in a form that is pure, active, and in a high yield.

The term 'active' referred to in relation to the biopolymer means that the biopolymers are not damaged or degraded in any way which may degrade the functions of the biopolymers.

From the foregoing it will be clear that biological sludge is the best starting material for biopolymer production since primary sludge is not a biopolymer source and would only add to the contaminant load which has to be removed. Nevertheless, for operational reasons, it may be more expedient to start the biopolymer preparation process with combined sludge as will be demonstrated later. In contrast, the preparation process is considerably simplified however where the biological sludge provides the feed stock for the biopolymer.

The term biopolymer fraction referred to herein relates to a fraction of biopolymers which have a similar molecular size or surface property taken from a population of biopolymers.

The purity of a biopolymer fraction may be defined as follows:

Purity=mass of biopolymer/total mass of the product

For biological sludge, the removal of the extracellular polymer substances (EPS) alone increases the purity of a biopolymer fraction by 100%, since the EPS typically account for 50% of the cell biomass. EPS may be removed by a number of mechanical means such as by using high shear rates. Alternatively, EPS may be removed by chemical means such as surfactant treatments or enzyme treatments. Digestion commonly achieves 50% EPS removal.

Numerous techniques are available for cell lysis (or bacterial cell wall disruption/rupture) including: high shear methods, high pressure methods and high temperature methods; as well as chemical and enzymatic means.

Suitable methods for disrupting or rupturing bacterial cell walls to release the intracellular content for use with the present invention include: ultra-sonication means, bead mills, and caustic treatment.

It should also be noted that bacterial cell wall disruption only causes the cells to fracture thereby releasing any intracellular content or exposing the intracellular content to possible chemical attacks, but leaving the crystalline structure of the cell wall relatively intact.

Biopolymer molecules are often partially crystalline (also referred to as semi-crystalline), with crystalline regions dispersed within amorphous material. Crystalline polymers are denser, more physically robust and more resistant to chemical attacks than amorphous polymers.

It is desirable to dissolve the intracellular contents without dissolving or generating very small cell wall fragments in order to conveniently separate the different intracellular materials by for example filtration.

In contrast, prolonged action on the bacterial cells by a bead mill (also known as a micro-mill) employing small beads of very high hardness such as ceramic beads, further reduces the size of the bacterial cell wall fragments. However, the bacterial cell wall fragments only swell if exposed to high pH conditions. Therefore, caustic treatment alone is not sufficient to achieve dissolution of the peptidoglycan. The dissolution of the peptidoglycan requires grinding of the cell fragments in a caustic media with ceramic beads. In contrast, nucleic acids are more readily soluble in a caustic media and often do not required any grinding action.

For specific applications, relatively pure DNA or pure peptidoglycan fractions are desirable. That is, DNA fractions at levels of at least 50% purity; more preferably at least 70% purity and most preferably at least 85% purity are desirable.

The separation of DNA from peptidoglycan may be achieved by first treating the cell lysate with anaerobic digestion conditions whereby all of the nucleic acids undergo gasification (that is, the nucleic acids are converted to biogas in the form of methane and $CO_2$) leaving the peptidoglycan relatively intact. Alternatively, any cell fragments may be separated from the soluble nucleic acids by filtering through a suitably rated filter.

It will be appreciated that the cell lysate or filtered lysate containing the soluble DNA and/or soluble peptidoglycan may also contain other soluble contaminants. Such contaminants may be conveniently separated from the biopolymers by selective precipitation of the biopolymers. For example, both DNA and peptidoglycan are 'poly-acids' which readily precipitate as the pH of solution drops. DNA and peptidoglycan are also susceptible to precipitation due to charge neutralisation with multivalent cations such as $Ca^{++}$ and $Mg^{++}$ ions.

DNA and peptidoglycan are also known as macro-molecules and may interact and bind with many different molecules. The ability of the macromolecules to bind different molecules makes the biopolymers valuable as agents for wastewater treatment.

It is also possible to alter or enhance their surface property to improve their binding of specific compounds with one or more suitable chemicals. Therefore, with suitable modifications the nucleic acids and peptidoglycans may be used as for example but not limited to: surface active agents, coagulants, flocculants, adsorbents, surface coatings, complexing agents. Chemical modification of the biopolymers with specific ligands may be conveniently carried out with staining and intercalating techniques.

In chemistry, intercalation is the reversible inclusion of a molecule (or group) between two other molecules (or groups). Examples include DNA intercalation and graphite intercalation compounds. There are several ways in which molecules (in this case, also known as ligands) may interact with DNA. For example, ligands may interact with DNA by: covalently binding; electrostatically binding; or intercalating. Intercalation occurs when ligands of an appropriate size and chemical nature insert between base pairs of DNA. These ligands are mostly polycyclic, aromatic, and planar, and therefore often make effective nucleic acid stains. Examples of DNA intercalators include: berberine, ethidium bromide, proflavine, daunomycin, doxorubicin, and thalidomide. DNA intercalators are used in chemotherapeutic treatment to inhibit DNA replication in rapidly growing cancer cells.

Staining is an auxiliary technique used in microscopy to enhance contrast in the microscopic image. Stains and dyes are frequently used in biology and medicine to highlight structures in biological tissues for viewing, often with the aid of different microscopes. Stains may be used to define and examine bulk tissues (highlighting, for example, muscle fibres or connective tissue), cell populations (classifying different blood cells, for instance), or organelles within individual cells.

In biochemistry there is also the requirement to add a class-specific (DNA, proteins, lipids, carbohydrates) dye to a substrate to qualify or quantify the presence of a specific compound. Staining and fluorescent tagging may serve similar purposes. Biological staining is also used to mark cells in flow cytometry, and to flag proteins or nucleic acids in gel electrophoresis. Certain stains are often combined to reveal more details and features than a single stain alone. Combined with specific protocols for fixation and sample preparation, scientists and physicians may use these standard techniques as consistent, repeatable diagnostic tools. A 'counterstain' is a stain that makes cells or structures more visible, when not completely visible with the principal stain. For example, crystal violet stains only gram-positive bacteria in gram staining. A safranin counterstain is applied that stains all cells, allowing identification of gram-negative bacteria.

In one embodiment of the present invention there is provided a method of preparing a DNA/peptidoglycan blend from sewage sludge in which the blend contains mainly DNA and peptidoglycan and which comprises the following steps:

1) removing extracellular polymeric substances (EPS) from bacterial cells in sewage sludge by anaerobic digestion;
2) rupturing/lysing the bacterial cell walls by at least 75% to release the intracellular contents of the bacterial cells using sodium hydroxide (NaOH) and milling to solubilise the DNA/RNA and other contaminants present;
3) precipitating the DNA onto the peptidoglycan debris using a suitable precipitant such as calcium chloride ($CaCl_2$);
4) removing the precipitate containing the DNA/peptidoglycan blend from the process liquor using a suitable solid liquid separation technique such as sedimentation or centrifugation.

In an alternative embodiment of the present invention there is provided a method of isolating peptidoglycan from sewage sludge which comprises the following steps:

1) optionally removing extracellular polymeric substances (EPS) from bacterial cells in sewage sludge by anaerobic digestion;
2) rupturing/lysing the bacterial cell walls by at least 75% to release the intracellular contents of the bacterial cells using sodium hydroxide (NaOH) and milling to solubilise the DNA RNA and other contaminants present;
3) removing DNA/RNA and other contaminants present including any EPS present from bacterial cells in sewage sludge by anaerobic digestion;
4) removing the peptidoglycan debris from the digestate using a suitable solid liquid separation technique such as filtration or centrifugation.

For a better understanding of the present invention and to show more clearly how it may be carried into effect, the following examples will now be discussed below.

EXAMPLE 1

Samples of biopolymer were prepared by milling samples of digested sludge cake followed by an extraction procedure as follows. (Digested sludge cake is the sludge solid fraction obtained by substantially removing the water from digested sludge).

A digested sludge cake with a typical dry mass content of 25% was milled using a Capco Ball Mill 12VS. The samples were processed for three days in an aqueous caustic environment in order to break down the cell structure. The milling took place in 500 ml bottles under the following conditions:

Sludge Cake 50 g (25% Dry Solids)
Distilled Water 150 ml
NaOH (Dry Mass) greater than 5%
Milling Time greater than 48 hours
Final pH 9.0
Milling Speed 100 rpm
Milling Media 2 mm $ZrO_2$ (200 ml)

The biopolymer was precipitated from out of the cell lysate by the addition of calcium chloride ($CaCl_2$) solution. A 20% solution of $CaCl_2$ to lysate in a ratio of 1:2 was used. The precipitate resulting from this operation was recovered by centrifugation and washed with distilled water before use as an extracted biopolymer.

The extracted biopolymer had a compacted but granular appearance with a dry solid content of 16.97% weight/weight (w/w). Initial analysis showed that the granules had a phosphorus (P) content of 6.5% weight/weight (w/w, dry basis) after treatment with the 20% solution of $CaCl_2$.

The extracted biopolymer purity was estimated to have a DNA content of 8% weight/weight (w/w dry basis).

EXAMPLE 2

A number of experiments were conducted to demonstrate the use of a biopolymer as an agent for the removal of orthophosphate (OP) from settled sewage. The typical OP levels for settled sewage at a test site were in the region of 2 mg/L, so for the purpose of the experiments the settled sewage was spiked with sodium di-hydrogen phosphate to bring the OP content up to a value of 20 mg/L.

A 'Jar' test protocol was then used which comprised a test in which to 500 ml of settled sewage were added varying amounts of crude biopolymer (in the form of cell lysate) followed by the addition of 20 ml of $CaCl_2$ solution (at 20%) with rapid mixing (200 rpm) for 1 minute. A 15-minute period was allowed for flocculation/coagulation followed by a settling period of 15 minutes before analysis.

Table 1 illustrates the results of contacting the biopolymer in the form of cell lysate with settled sewage. The 'Jar-test' protocol indicated a varying degree of orthophosphate removal depending on the amount of the crude biopolymer (cell lysate) added to the test mixture. The results are shown in Table 1 which illustrates the effectiveness of crude biopolymer in phosphorus removal from wastewater.

TABLE 1

| Amount of cell lysate added (mL) | Total System OP (mg) | Residual OP (mg/L) | Total System Ca (mg) | Ca P Ratio (w/w) | Settled Sewage OP Removal % |
|---|---|---|---|---|---|
| 5 | 13.3 | 7.4 | 103 | 7.8 | 62 |
| 10 | 16.8 | 2.9 | 206 | 12.3 | 85 |
| 15 | 20.3 | 1.4 | 309 | 15.2 | 93 |
| 20 | 23.8 | 1.4 | 412 | 17.3 | 93 |

OP—orthophosphate

EXAMPLE 3

The protocol outlined in example 2 was followed except that in example 3 the crude biopolymer in the form of cell lysate was replaced by 10 g of extracted biopolymer and no $CaCl_2$ was added. The settled sewage was also replaced with sludge liquor with orthophosphate (OP) content up to about 100 mg/L and with varying amounts of volatile fatty acids (VFA) present.

The results of the biopolymer trials using the sludge liquor containing orthophosphate are shown in Table 2.

Table 2 illustrates the effectiveness of the extracted biopolymer in phosphorus removal from sludge liquor.

TABLE 2

| Sample (Added VFA mg/L) | Residual OP (mg P/L) | OP Removal (%) | Residual Calcium (mg/L) | pH |
|---|---|---|---|---|
| 200 | 11.8 | 85.0 | 1542 | 6.8 |
| 300 | 25.7 | 72.7 | 1602 | 6.3 |
| 400 | 37.9 | 56.5 | 1472 | 6.0 |
| 500 | 49.4 | 48.5 | 1548 | 5.6 |
| 600 | 55.0 | 43.0 | 1572 | 5.5 |

It will be appreciated that many modifications and enhancements may be made to the basic method and product outlined herein.

For instance, the methods of separating DNA from peptidoglycan or other contaminants; and of precipitating the biopolymers may be varied, for example by pH adjustment or by adding salts similar to $CaCl_2$ or even organic solvents.

Other possible modifications will be readily apparent to the appropriately skilled person.

What is claimed is:

1. A method of removing phosphorus from wastewater comprising:
   i) removing extracellular polymeric substances (EPS) from bacterial cells in sewage sludge to provide an EPS-removed sewage sludge;
   ii) disrupting bacterial cell walls of the bacterial cells present in the EPS-removed sewage sludge by at least 75% to release intracellular contents of the bacterial cells so as to form a cell lysate;
   iii) separating the biopolymers or biopolymer fractions from any contaminants present, wherein step i) is performed before steps ii) and iii);
   iv) adding the isolated biopolymers or biopolymer fractions to said wastewater; and
   v) allowing said isolated biopolymers or biopolymer fractions to remove said phosphorus from the wastewater.

2. The method according to claim 1, wherein the method of isolating the biopolymers or biopolymer fractions further comprises the step of:
   precipitating the soluble biopolymers from the cell lysate prior to separating the biopolymers from any contaminants present.

3. The method according to claim 2 wherein the soluble biopolymers precipitated comprise nucleic acids.

4. The method according to claim 1 wherein the cell lysate is anaerobically digested and peptidoglycan present in the cell lysate is separated and isolated.

5. The method according to claim 1 wherein the sewage sludge is a biological sludge.

6. The method according to claim 1 wherein the ruptured bacterial cell walls are ground to disperse or dissolve peptidoglycan present therein.

7. The method according to claim 1 wherein the extracellular polymeric substances (EPS) are removed using a mechanical means.

8. The method according to claim 1 wherein the extracellular polymeric substances (EPS) are removed using a chemical means.

9. The method according to claim 1 wherein the extracellular polymeric substances (EPS) are removed using enzyme treatments.

10. The method according to claim 1 wherein the bacterial cell walls are disrupted by means of one or more of: ultra-sonication, and/or bead mills, and/or caustic treatments.

11. The method according to claim 1 wherein peptidoglycan present in the cell lysate is separated and isolated from the cell DNA.

12. The method according to claim 11 wherein the cell lysate is anaerobically digested.

13. The method according to claim 11 wherein the cell lysate is filtered.

14. The method according to claim 2 wherein the biopolymers are treated before, during or post the precipitation step with one or more chemicals.

15. The method according to claim 1, wherein the extracellular polymeric substances (EPS) are removed by at least 50%.

16. The method according to claim 1, wherein the extracellular polymeric substances (EPS) are removed by anaerobic digestion.

17. The method according to claim 16, wherein the extracellular polymeric substances (EPS) are removed by at least 50%.

18. A method of preparing and separating biopolymers from sewage sludge; and subsequently using said biopolymers to remove phosphorus from wastewater in a method comprising adding biopolymers to said wastewater, and allowing said biopolymers to remove said phosphorus from the wastewater; wherein the biopolymers are prepared and separated by the following steps:
   i) removing extracellular polymeric substances (EPS) from bacterial cells in sewage sludge to provide an EPS-removed sewage sludge;
   ii) disrupting the bacterial cell walls of bacteria present in the EPS-removed sewage sludge by at least 75% to release the intracellular contents of the bacterial cells; and
   iii) separating the biopolymers from any contaminants present, wherein step i) is performed before step ii), and wherein step (ii) is performed before step iii).

19. A method of removing phosphorus from wastewater comprising:
   i) removing extracellular polymeric substances (EPS) from bacterial cells in sewage sludge by anaerobic digestion to provide an EPS-removed sewage sludge;
   iia) disrupting bacterial cell walls of the bacterial cells present in the EPS-removed sewage sludge by at least 75% to release intracellular contents of the bacterial cells so as to form a cell lysate and solubilising nucleic acids and contaminants present in the cell lysate;
   iib) precipitating the nucleic acids onto peptidoglycan debris present in the cell lysate to provide a precipitate comprising a blend of the nucleic acids and the peptidoglycan debris;

iii) separating the biopolymers or biopolymer fractions from any contaminants present, wherein the biopolymers or biopolymer fractions comprise a blend of nucleic acids and peptidoglycan and wherein step i) is performed before steps iia), iib) and iii);

iv) removing the precipitate from the cell lysate using a solid liquid separation technique;

v) adding the removed precipitate to said wastewater; and vi) allowing the removed precipitate to remove said phosphorus from the wastewater.

20. A method of removing phosphorus from wastewater comprising:

i) removing extracellular polymeric substances (EPS) from bacterial cells in sewage sludge to provide an EPS-removed sewage sludge;

ii) disrupting bacterial cell walls of the bacterial cells present in the EPS-removed sewage sludge by at least 75% to release intracellular contents of the bacterial cells so as to form a cell lysate and solubilising nucleic acids and contaminants present in the cell lysate;

iii) removing the nucleic acids, any EPS present, and the contaminants present in the cell lysate by anaerobic digestion; before removing peptidoglycan debris present in the digestate formed by the anaerobic digestion using a solid liquid separation technique to provide biopolymer fractions, wherein step i) is performed before steps ii) and iii);

iv) adding the biopolymer fractions to said wastewater; and v) allowing the biopolymer fractions to remove said phosphorus from the wastewater.

21. The method of claim 19, wherein the extracellular polymeric substances (EPS) are removed by at least 50%.

22. The method of claim 19, wherein the precipitate is a blend of nucleic acids and peptidoglycan with a purity of at least 50%.

23. The method of claim 21, wherein the precipitate is a blend of nucleic acids and peptidoglycan with a purity of at least 50%.

24. The method of claim 20, wherein the extracellular polymeric substances (EPS) are removed by at least 50%.

25. The method of claim 20, wherein the peptidoglycan debris has a purity of at least 50%.

26. The method of claim 24, wherein the peptidoglycan debris has a purity of at least 50%.

* * * * *